United States Patent
Silks et al.

(10) Patent No.: US 9,469,574 B2
(45) Date of Patent: Oct. 18, 2016

(54) CONVERSION OF OLIGOMERIC STARCH, CELLULOSE, OR SUGARS TO HYDROCARBONS

(75) Inventors: Louis A. Silks, Los Alamos, NM (US); Andrew Sutton, Los Alamos, NM (US); Jin Kyung Kim, Daejeon (KR); John Cameron Gordon, Los Alamos, NM (US); Ruilian Wu, Los Alamos, NM (US); David B. Kimball, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 96 days.

(21) Appl. No.: 14/413,552

(22) PCT Filed: Sep. 14, 2012

(86) PCT No.: PCT/US2012/055337
§ 371 (c)(1),
(2), (4) Date: Apr. 22, 2015

(87) PCT Pub. No.: WO2014/011199
PCT Pub. Date: Jan. 16, 2014

(65) Prior Publication Data
US 2015/0251969 A1  Sep. 10, 2015

Related U.S. Application Data

(60) Provisional application No. 61/669,980, filed on Jul. 10, 2012.

(51) Int. Cl.
*C07H 3/02* (2006.01)
*C07C 1/207* (2006.01)
*C10G 3/00* (2006.01)
*C07D 307/46* (2006.01)

(52) U.S. Cl.
CPC ........... *C07C 1/2076* (2013.01); *C07D 307/46* (2013.01); *C07H 3/02* (2013.01); *C10G 3/47* (2013.01); *C10G 3/50* (2013.01); *C07C 2521/18* (2013.01); *C07C 2523/42* (2013.01); *C07C 2527/11* (2013.01); *C07C 2531/28* (2013.01); *Y02P 30/20* (2015.11)

(58) Field of Classification Search
None
See application file for complete search history.

(56) References Cited

U.S. PATENT DOCUMENTS

| | | |
|---|---|---|
| 2009/0139134 A1* | 6/2009 | Yoshikuni ................. C12P 5/02 44/307 |
| 2010/0228067 A1 | 9/2010 | Peterson et al. |
| 2011/0312050 A1 | 12/2011 | Zhang et al. |
| 2011/0312487 A1 | 12/2011 | Chen et al. |
| 2011/0312488 A1 | 12/2011 | Chen et al. |

OTHER PUBLICATIONS

Blommel et al. Oligosaccharide Oligosaccharide Oligosaccharide, Aug. 25, 2008, retrieved from http ://www.biofuelstp.eu/downloadsNirent_Technology_Whitepaper.pdf.

* cited by examiner

*Primary Examiner* — Tam M Nguyen
(74) *Attorney, Agent, or Firm* — Lewis Roca Rothgerber Christie LLP

(57) ABSTRACT

The present invention is directed to the one step selective conversion of starch, cellulose, or glucose to molecules containing 7 to 26 contiguous carbon atoms. The invention is also directed to the conversion of those intermediates to saturated hydrocarbons. Such saturated hydrocarbons are useful as, for example, fuels.

12 Claims, 1 Drawing Sheet

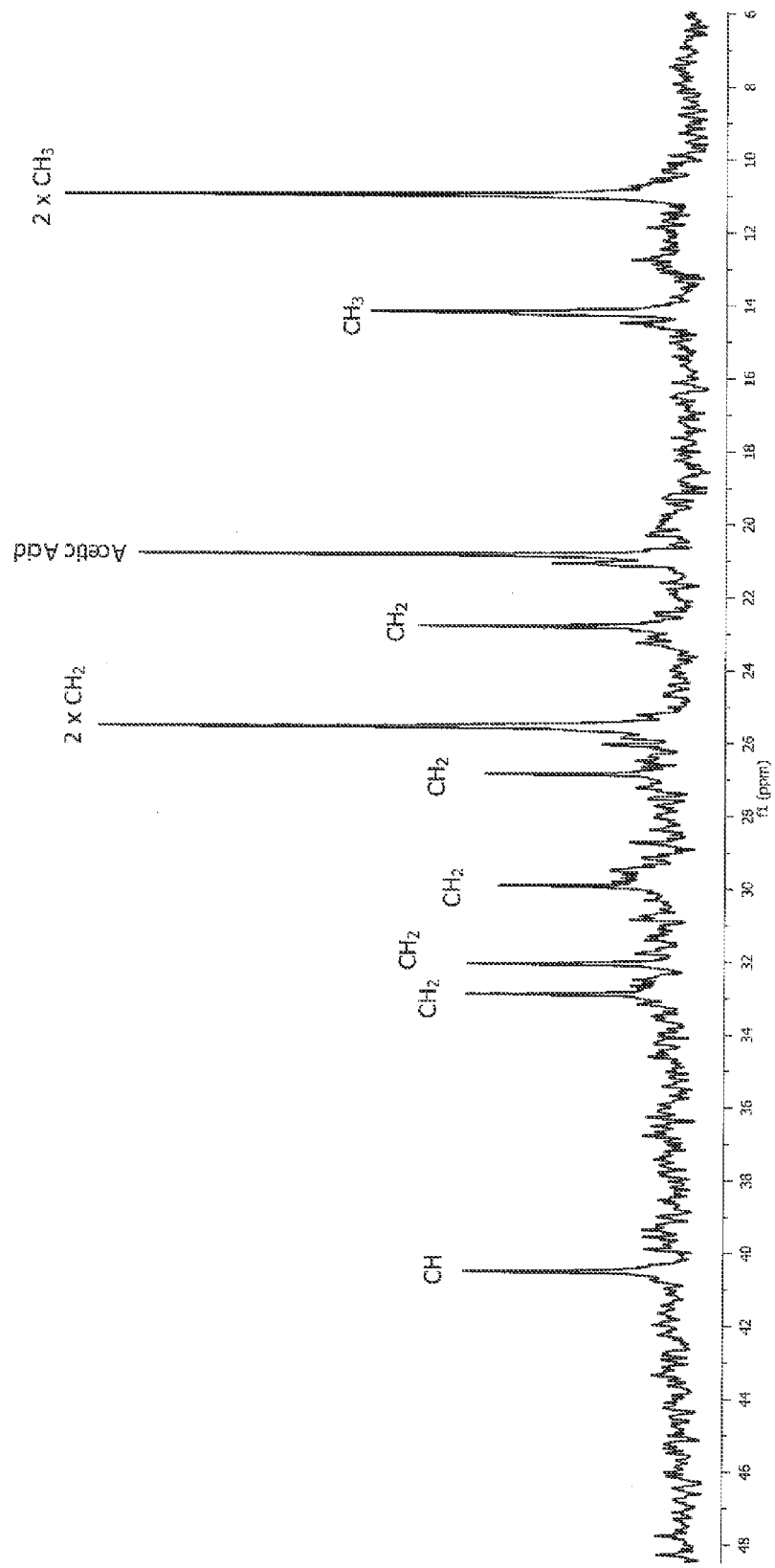

CONVERSION OF OLIGOMERIC STARCH, CELLULOSE, OR SUGARS TO HYDROCARBONS

CROSS-REFERENCE TO RELATED APPLICATIONS

This application is the National Stage of International Application No. PCT/US2012/055337, filed Sep. 14, 2012, which claims the benefit of priority of U.S. Provisional Application No. 61/669,980, filed Jul. 10, 2012, the entire disclosures of which are incorporated herein by reference.

GOVERNMENT RIGHTS

The United States government has rights in this invention pursuant to Contract No. DE-AC52-06NA25396 between the United States Department of Energy and Los Alamos National Security, LLC for the operation of Los Alamos National Laboratory.

TECHNICAL FIELD

The present invention is directed to the one step selective conversion of starch, cellulose, or glucose to molecules containing 7 to 26 contiguous carbon atoms. The invention is also directed to the conversion of those intermediates to saturated hydrocarbons. Such saturated hydrocarbons are useful as, for example, fuels.

BACKGROUND

Saturated hydrocarbons containing from about seven to about sixteen carbons, up to about twenty-six carbons, are used as fuels, as well as other materials. Such hydrocarbons are typically extracted or generated from petroleum, a non-renewable resource. Methods of generating fuel- and high-quality hydrocarbons from renewable sources are thus needed.

SUMMARY

The present invention is directed to processes for preparing saturated hydrocarbons comprising heating an oligosaccharide under acidic conditions for time sufficient to form a depolymerized oligosaccharide mixture; adding a suitable metal catalyst and a dicarbonyl to the depolymerized oligosaccharide mixture under conditions to yield an intermediate mixture; and adding hydrogen and a suitable hydrogenation catalyst to said intermediate mixture under suitable conditions to yield the saturated hydrocarbon.

BRIEF DESCRIPTION OF THE DRAWINGS

FIG. 1 depicts the NMR spectra from an unpurified product of example 2(a), an embodiment of the invention.

DETAILED DESCRIPTION OF ILLUSTRATIVE EMBODIMENTS

Oligosaccharides such as starch, cellulose, hemicelluloses, chitin, and cotton are abundant and easily obtainable materials that can be potentially used as precursors for fuels and chemical feedstocks. But to access the sugar molecule building blocks, i.e., 5- or 6-carbon containing units, located within these biopolymers and to transform them into useful fuel precursors, depolymerization followed by chain extension is needed. The present invention is directed to methods for readily performing these transformations.

In the present invention a suitable oligosaccharide can be converted to a saturated hydrocarbon in a process, with or without isolation of intermediate products. In one aspect of the present invention, the process of converting an oligosaccharide to a saturated hydrocarbon is achieved in a single pot or reaction vessel without isolation of any intermediate products.

As used herein, "saturated hydrocarbon" refers to organic compounds comprising saturated, straight or branched chain alkane moieties. Preferred saturated hydrocarbons of the invention include 7-26 carbon atoms, preferably 7-16 carbon atoms. One particularly preferred saturated hydrocarbon is 3-ethylnonane.

As used herein, "intermediate mixture" refers to a compound or mixture of compounds derived from processes of the invention, i.e., combining depolymerized oligosaccharide mixtures with dicarbonyls. The intermediate mixtures of the invention can contain 7 to 26 contiguous carbon atoms, preferably 7-16 contiguous carbon atoms. Within the scope of the invention, intermediate mixtures can also include additional moieties, for example, esters. The addition of such moieties does not contribute to the contiguous carbon count of the resulting saturated hydrocarbons of the invention.

As used herein, "starch" refers to an oligosaccharide comprising glucose units.

As used herein, "triflate", also referred to as trifluoromethanesulfonate, is a group with the formula $[CF_3SO_3]^-$. As used herein, the group $[CF_3SO_3]^-$ may also be designated as "OTf."

As used herein "oligosaccharides" are compounds including more than one saccharide molecule. Oligosaccharides within the scope of the invention include starch, cellulose, hemicelluloses, glucose, cellobiose, chitin, and cotton. "Oligosaccharides" of the invention also include compounds comprising monomeric building blocks derived from sugars such as 2-amino glucose, galactose, xylose, and the like. Disaccharides are within the scope of the oligosaccharides of the invention.

As used herein, "Lewis acids" are substances that are electron-pair acceptors. Examples of Lewis acids are known in the art and include $La(OTf)_3$, $Fe(OTf)_3$, $CeCl_3$, $ZnCl_2$, $ZrCl_4$, $BiCl_3$, $Sc(OTf)_3$, $Y(OTf)_3$, $La(OTf)_3$, and $Fe(OTf)_3$.

As used herein, "Brønsted acids" are substances that are able to donate a proton. Examples of Brønsted acids are known in the art.

In a first step, an oligosaccharide, for example, starch, is heated under conditions to yield a depolymerized oligosaccharide mixture. Such heating can be provided by, for example, heating at reflux or by microwave heating. The heating is preferably conducted under acidic conditions such as those provided by the addition of dilute hydrochloric acid, triflic acid, acetic acid, trifluoroacetic acid, or a combination thereof. Lewis acids or Brønsted acids can also be added to the heating step. Use of mixtures of acids during the heating step to form the depolymerized oligosaccharide mixture are also within the scope of the invention.

Alternatively, thermally stable amylases or cellulases, or room temperature depolymerization with native enzymes, can be used to depolymerize the oligosaccharide mixture.

Within the scope of the invention, the depolymerized oligosaccharide mixture is combined with a dicarbonyl to form an intermediate mixture. Preferred dicarbonyls for use in the invention include methyl acetoacetate, ethyl acetoacetate (EAA), iso-propyl acetoacetate (i-PrAA), 2,4-pentanedione (PD), n-propyl acetoacetate, esters of cyanoacetate, esters of malonate, and the like, as well as mixtures thereof. 2,4-pentanedione is particularly preferred.

The combination of the depolymerized oligosaccharide mixture with the dicarbonyl to form the intermediate mixture can optionally be conducted in the presence of a catalyst, for example a Lewis acid catalyst or a Brønsted acid catalyst, although any suitable acid catalyst can be used in the processes of the invention. Particularly preferred Lewis acids include, for example, Lewis acids of the formula $Ln(X)_n$ wherein Ln is a lanthanoid; X is halide, triflate, bis(triflamide), $C_{1-6}$ alkyl, aryl, amine, oxide, $C_{1-6}$ alkoxide, or aryloxide; and n is 2 or 3. Preferred Lewis acids are $La(OTf)_3$ and $Fe(OTf)_3$. Other Lewis acids for use in the invention include $CeCl_3$, $ZnCl_2$, $ZrCl_4$, and $BiCl_3$. The Lewis acids of the invention can also include a rare earth triflate. Examples of rare earth triflates that may be used in accordance with the present invention include $Sc(OTf)_3$, $Y(OTf)_3$, and $La(OTf)_3$, with lanthanum triflate being particularly preferred. Another preferred triflate is $Fe(OTf)_3$. Additional Lewis acids may be used in the present invention and are well known to those skilled in the art.

The combination of the depolymerized oligosaccharide mixture with the dicarbonyl to form the intermediate mixture can also be conducted in the presence of acids such as triflic acid (trifluoromethanesulfonic acid) and HCl. Such acids have been found useful in forming the intermediate mixture.

Preferably, the formation of the intermediate mixture is achieved in the presence of cerium chloride, iron chloride, indium chloride, bismuth chloride, lanthanum triflate, zirconium triflate, copper triflate, iron triflate, or a mixture thereof. In exemplary embodiments, the formation of the intermediate mixture is achieved in the presence of cerium chloride, iron chloride, lanthanum triflate, iron triflate, or a mixture thereof.

Conversion from the intermediate mixture to the saturated hydrocarbon can be accomplished by hydrogenation of the intermediate mixture and can be carried out with a suitable hydrogenation catalyst, for example, palladium on carbon (Pd/C). A suitable acid, for example acetic acid, hydrochloric acid, triflic acid, preferably triflic acid or hydrochloric acid, can be added. It is preferred that the reaction mixture be aqueous. Those skilled in the art can readily identify suitable reaction temperatures using routine experimentation. For example, the hydrogenation can be achieved at room temperature or above room temperature. Preferably, the hydrogenation reaction can be accomplished at temperatures of about 200° C. to 250° C. under a hydrogen atmosphere.

Preferred hydrogenation catalysts include those comprising palladium, platinum, iron, cobalt, copper, chromium, nickel, or mixture thereof. Catalysts comprising these metals are known in the art. A preferred catalyst is Pd/C. The skilled person can determine a suitable amount of catalyst needed to perform the methods of the invention by routine experimentation.

During hydrogenation, the hydrogen can be supplied at either atmospheric pressure at pressures above atmospheric pressure. Preferred pressures of hydrogen are from about 15 psi to about 500 psi, with about 100 psi being preferred.

The skilled person can readily determine appropriate temperatures for the steps of the invention without undue experimentation. Temperatures from about ambient temperature to about 250° C. are preferred, with temperatures from about 200° C. to 250° C. being particularly preferred for the hydrogenation methods.

Oligosaccharide Conversion to Branched Alkanes

Coupling can be performed using a variety of oligosaccharides and diketones to give the general (furan) intermediate mixture A shown in Scheme 1. Scheme 1 is general and applicable to all combinations of the invention. Starch extracted directly from a Russet potato and treated by the procedures of the invention yielded identical products and reactivity.

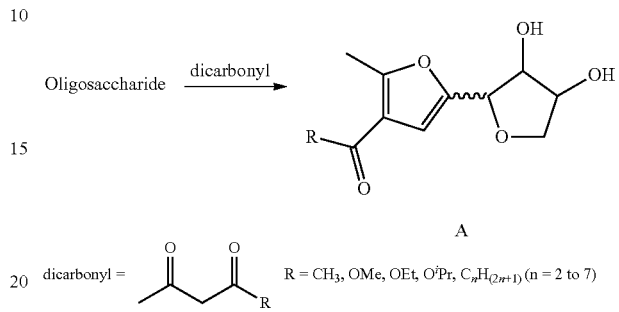

The following examples are illustrative only and are not intended to be construed as limiting of the invention.

EXAMPLE 1

Preparation of 1-(5-(3,4-dihydroxytetrahydrofuran-2-yl)-2-methylfuran-3-yl)ethanone (1).

To a 2-neck round bottom flask equipped with a thermometer and reflux condenser was charged with starch (1.00 g, 9.25 mmol according to molecular weight 162.12) and 0.1 M hydrochloric acid (10.0 mL). The mixture was heated to 90-95° C. for 24 hours. The mixture was removed from heat, and to this was added cerium chloride heptahydrate (0.186 g, 0.500 mmol), EtOH (22.5 mL) and 2,4-pentanedione (0.617 g, 0.63 mL, 6.17 mmol). The mixture was then heated again at 70-75° C. for 48 h. The solvent was removed by rotary evaporation and the residue was purified on silica gel with 50% EtOAc/hexanes to provide 0.890 g (64%) of 1-(5-(3,4-dihydroxy-tetrahydrofuran-2-yl)-2-methylfuran-3-yl)ethanone as a light yellow solid $^1$H NMR (CDCl$_3$) δ 6.61 (s, 1 H), 4.66 (d, J=6.7 Hz, 1 H), 4.49-4.33 (m, 2 H), 4.27 (dd, J=10.1, 4.7 Hz, 1 H), 3.90 (dd, J=10.1, 2.9 Hz, 1 H), 2.58 (s, 3 H), 2.39 (s, 3 H).

EXAMPLES 2(a)-2(e)

Conversion of (1) into 3-ethylnonane

Method (a). Compound (1) (0.200 g, 0.885 mmol) was dissolved in glacial acetic acid (5 mL) and added along with Pd/C (0.100 g, 5 wt. % Pd, 0.005 g Pd, 5.30 mol % Pd) and La(OTf)$_3$ (0.100 g, 0.171 mmol, 19.0 mol % La) to a stainless steel Swagelok sample tube. The tube was then pressurized with 100 psi H$_2$ and heated to 225° C. for 14 hours. Upon cooling, the pressure was released and reaction mixture extracted from the vessel with methylene chloride (2×1 mL) and water (2×1 mL). The combined layers were filtered and the organic layer separated, dried over NaSO$_4$ and solvent removed in vacuo to yield 3-ethylnonane as a colorless oil (0.102 g, 85%). $^{13}$C NMR (101 MHz, CDCl$_3$) δ 40.54 (CH), 32.92 (CH$_2$), 32.08 (CH$_2$), 29.94 (CH$_2$), 26.87 (CH$_2$), 25.58 (2×CH$_2$), 22.82 (CH$_2$), 14.20 (CH$_3$), 11.01 (2×CH$_3$). $^1$H NMR (400 MHz, CDCl$_3$) δ 4.10 (m, 1 H), 1.25 (m, 14 H), 0.82 (m, 9 H).

Method (b). Compound (1) (0.200 g, 0.885 mmol) was dissolved in 1M HOTf (5 mL) and added along with Pd/C (0.100 g, 5 wt. % Pd, 0.005 g Pd, 5.30 mol % Pd). The tube was then pressurized with 100 psi $H_2$ and heated to 225° C. for 14 hours. Upon cooling, the pressure was released and reaction mixture extracted from the vessel with methylene chloride (2×1 mL) and water (2×1 mL). The combined layers were filtered and the organic layer separated, dried over $NaSO_4$ and solvent removed in vacuo to yield 3-ethylnonane as a colorless oil.

Method (c). Compound (1) (0.200 g, 0.885 mmol) was dissolved in 0.1M HOTf (trifluoromethane sulfonic acid, 5 mL) and added along with Pd/C (0.100 g, 5 wt. % Pd, 0.005 g Pd, 5.30 mol % Pd). The tube was then pressurized with 100 psi $H_2$ and heated to 225° C. for 14 hours. Upon cooling, the pressure was released and reaction mixture extracted from the vessel with methylene chloride (2×1 mL) and water (2×1 mL). The combined layers were filtered and the organic layer separated, dried over $NaSO_4$ and solvent removed in vacuo to yield 3-ethylnonane as a colorless oil.

Method (d). Compound (1) (0.200 g, 0.885 mmol) was dissolved in 1M HCl (hydrochloric acid, 5 mL) and added along with Pd/C (0.100 g, 5 wt. % Pd, 0.005 g Pd, 5.30 mol % Pd). The tube was then pressurized with 100 psi $H_2$ and heated to 225° C. for 14 hours. Upon cooling, the pressure was released and reaction mixture extracted from the vessel with methylene chloride (2×1 mL) and water (2×1 mL). The combined layers were filtered and the organic layer separated, dried over $NaSO_4$ and solvent removed in vacuo to yield 3-ethylnonane as a colorless oil.

Method (e). Compound (1) (0.200 g, 0.885 mmol) was dissolved in glacial acetic acid (5 mL) and added along with Pd/C (0.100 g, 5 wt. % Pd, 0.005 g Pd, 5.30 mol % Pd) and $Fe(OTf)_3$ (0.100 g, 0.283 mmol) to a stainless steel Swagelok sample tube. The tube was then pressurized with 100 psi $H_2$ and heated to 225° C. for 14 hours. Upon cooling, the pressure was released and reaction mixture extracted from the vessel with methylene chloride (2×1 mL) and water (2×1 mL). The combined layers were filtered and the organic layer separated, dried over $NaSO_4$ and solvent removed in vacuo to yield 3-ethylnonane as a colorless oil.

EXAMPLE 3

One Pot Preparation of 3-ethylnonane

A 300 mL stainless steel Parr reactor equipped with thermal and pressure control system was charged with 1.00 g (9.25 mmol) starch (using the molecular weight 162.12 g/mol based on molecular weight of glucose), 20 mL of $H_2O$, and triflic acid (final concentration, 0.1 M). The mixture was stirred and heated to 90-95° C. for 24 hours. Cerium chloride heptahydrate (0.186 g, 0.5 mmol), EtOH (22.5 mL) and 2,4-pentanedione (0.617 g, 0.63 mL, 6.17 mmol) was added and the temperature was maintained at 90-95° C. for 48 h. At this point Pd/C (0.100 g, 10 wt. % Pd) is added. The mixture was degassed (3×) and pressurized with 100 psi $H_2$ and was heated to 225° C. for 14 hours. Upon cooling, the pressure was released and reaction mixture extracted from the vessel with methylene chloride (2×1 mL) and water (2×1 mL). The combined layers were filtered and the organic layer was separated, dried over $NaSO_4$ and solvent removed in vacuo to yield 3-ethylnonane as a colorless oil.

EXAMPLE 4

Various experimental conditions were employed for the conversion of starch into (furan) intermediate molecules, with results and conditions for different conditions illustrated below in Table 2. The general procedure involved combining starch with a metal catalyst (mol % of catalyst relative to dicarbonyl donor) in water, heating this mixture in a microwave reactor to release glucose monomers from the starch polysaccharide chains, then adding a dicarbonyl donor to the reaction and further heating either in the microwave reactor or under reflux. The yields reported in Table 2 are obtained either after product isolation via chromatography or determined directly using liquid chromatography mass spectrometry (LCMS). For the LCMS method, an aliquot is taken from the reaction mixture and combined with a known concentration of $^{13}C_6$ enriched intermediate molecules made independently using $^{13}C_6$ glucose such that comparison of the two molecular ion peaks (M+1 vs. M+7) in the LCMS allows for quantitative determination of product yield.

Tables 2 and 3 demonstrate various outcomes using lanthanum triflate, cerium chloride or iron chloride as catalysts. The dicarbonyl donor was selected from ethyl acetoacetate (EAA), isopropyl acetoacetate (i-PrAA), or 2,4-pentanedione (PD). It is preferred that the starch be hydrolyzed prior to condensation with the donor. Optimal conditions resulted from the combination of 10 mol % $CeCl_3$, EAA, starch (excess; 1.25 equiv), and a microwave reaction temperature of 140° C. for 48 h.

TABLE 2

Depolymerization of starch using a Lanthanide or Fe catalyst, by microwaving at 140° C. for 1.5 h before combining with donor and additional heating.

| Using 1.25 equiv | Donor | Catalyst/ Loading | Conditions | Product Yield |
|---|---|---|---|---|
| Starch | EAA | 2.5% $La(OTf)_3$ | Reflux w EtOH 72 h | 32%, LCMS |
| Starch | EAA | 10% $La(OTf)_3$ | 140° C. 1.5 h w $H_2O$ | 12%, LCMS |
| Starch | EAA | 10% $CeCl_3$ | 140° C. 1.5 h w $H_2O$ | 30%, LCMS |
| Starch | iPrAA | 10% $CeCl_3$ | 140° C. 1.5 h w $H_2O$ | 35%, Isolated |
| Starch | EAA | 10% $CeCl_3$ | Reflux w $H_2O$ 48 h | 40%, LCMS |
| Starch | iPrAA | 10% $CeCl_3$ | Reflux w $H_2O$ 48 h | 35%, LCMS |
| Starch | PD | 25% $FeCl_3$ | Reflux w $H_2O$ 24 h | 15%, Crude |
| Starch | PD | 25% $FeCl_3$ 1st recycle | Reflux w $H_2O$ 24 h | 30%, Crude |

EXAMPLE 5

Table 3 shows the production of glucose from starch hydrolysis/depolymerizarion with various lanthanide containing catalysts using a microwave reactor at 140° C. for various durations.

TABLE 3

Conversion of starch to glucose.

| Catalyst/Loading | Conditions | Yield of Glucose |
|---|---|---|
| 2.5% $La(OTf)_3$ | 140 C. 3 h 30 min in $H_2O$ | 51% LCMS |
| 5% $La(OTf)_3$ | 140 C. 3 h in $H_2O$ | 42.2% LCMS |
| 10% $La(OTf)_3$ | 140 C. 3 h in $H_2O$ | 45.6% LCMS |

TABLE 3-continued

Conversion of starch to glucose.

| Catalyst/Loading | Conditions | Yield of Glucose |
|---|---|---|
| 20% La(OTf)$_3$ | 140 C. 3 h in H$_2$O | 57% LCMS |
| 10% CeCl$_3$ | 140 C. 2 h in H$_2$O | 55% LCMS |

EXAMPLE 6

Table 4 illustrates that starch hydrolysis/depolymerization can be performed concurrently with the condensation reaction.

TABLE 4

Results of concurrent starch hydrolysis/depolymerization into glucose and conversion into C$_{11}$ product

| Starting Material | Donor | Catalyst Loading | Temperature | Microwave Time | Total Conversion | Product yield* |
|---|---|---|---|---|---|---|
| Starch | PD | 10 mol % CeCl$_3$•7H$_2$O | 130° C. | 3.5 hrs | No rxn | |
| Starch | PD | 10 mol % CeCl$_3$•7H$_2$O | 150° C. | 3.5 hrs | 83% | 33% |
| Starch | PD | 20 mol % CeCl$_3$•7H$_2$O | 150° C. | 3.5 hrs | NA | |

*product yield determined by NMR spectroscopy

EXAMPLE 7

Table 5 shows the effect of different concentrations of CeCl$_3$ and reaction time on yields of products that result from reaction of glucose with EAA or glucose with iPrAA

TABLE 5

Outcome of reactions of glucose with EAA or glucose with iPrAA in the presence of CeCl$_3$•7H$_2$O (catalyst loading relative to Glucose)

| Starting Material | Donor | Catalyst Loading | Temperature | Microwave Time | Total Conversion | Product yield* |
|---|---|---|---|---|---|---|
| Glucose | EAA | 25 mol % CeCl$_3$•7H$_2$O | 100° C. | 6.5 hrs | 56% | 41% |
| Glucose | iPrAA | 25 mol % CeCl$_3$•7H$_2$O | 100° C. | 6.5 hrs | 72% | 43% |
| Glucose | iPrAA | 25 mol % CeCl$_3$•7H$_2$O | 110° C. | 5 hrs | 58% | 48% |
| Glucose | iPrAA | 40 mol % CeCl$_3$•7H$_2$O | 100° C. | 4 hrs | 57% | 26% |
| Glucose | iPrAA | 55 mol % CeCl$_3$•7H$_2$O | 100° C. | 4 hrs | 50% | 31% |
| Glucose | iPrAA | 25 mol % CeCl$_3$•7H$_2$O | 100° C. | 4 hrs | 34% | 22% |
| Glucose | iPrAA | 25 mol % CeCl$_3$•7H$_2$O | 100° C. | 4 hrs | 48% | 24% |

*product yields determined from NMR spectra

EXAMPLE 8

Table 6 shows that starch can be converted in reasonable yields into the corresponding furan intermediates using cerium chloride as the catalyst. Depolymerizing the starch via microwave promotion is carried out first, followed by then reflux in the presence of the ketone donor at 97° C. for 48 h. Additionally, when starch isolated from a russet potato was used, coupling with PD resulted in the corresponding C$_{11}$ adduct in 36% yield (based on the potato containing 50% starch). Mathews, K. R., Landmark, J. D., Stickle, D. F., J. Chem. Ed. 2004, 81, 702.

TABLE 6

Starch depolymerized in microwave 2 hrs at 140° C., and heat at reflux.

| Using 1.5 equiv | Donor | Catalyst Loading | Total Conversion | Product Yield* |
|---|---|---|---|---|
| Starch | iPrAA | 25 Mol % CeCl$_3$•7H$_2$O | 100% | 61% |
| Starch | iPrAA | 50 Mol % CeCl$_3$•7H$_2$O | 100% | 68% |
| Starch | iPrAA | Recycled 50 Mol % CeCl$_3$•7H$_2$O | 100% | 65% |
| Potato Starch | PD | 25 mol % CeCl$_3$•7H$_2$O | 50% | 36% |

*product yields determined by NMR spectroscopy

EXAMPLE 9

Table 7 shows the effect of conventional heating (i.e. no microwaving) in various solvent and solvent mixtures on the CeCl$_3$ catalyzed reaction between starch and PD under acidic conditions. A slight excess of starch to PD was used and the product yields are listed as isolated, purified yields.

TABLE 7

Conventional heating of starch in the presence of PD.

| solvent | catalyst | Temperature (24 h) | yield (%) |
|---|---|---|---|
| 0.25M HCl | CeCl$_3$•7H$_2$O, Na$_2$MoO$_4$ | 80-90° C. | 24 |
| 0.25M HCl | FeCl$_3$ | 83-85° C. | 5 |
| 0.05% w/w HCl | CeCl$_3$•7H$_2$O | 90-95° C. | NR |
| 0.1M HCl-EtOH (1:2) | CeCl$_3$•7H$_2$O (9%) | 90-95° C. | 42% |
| 0.25M HCl-EtOH | CeCl$_3$•7H$_2$O | 70-75° C. | NR |
| 0.1M HCl | CeCl$_3$•7H$_2$O (20%) | 90-95° C. | 17% |
| 0.1M HCl | CeCl$_3$•7H$_2$O (8%) | 90-95° C. | 24% |
| 0.1M HCl-EtOH (1:1) | CeCl$_3$•7H$_2$O (8%) | 90-95° C. (48 h) | 44% |
| 1M HCl-EtOH (1:1) | CeCl$_3$•7H$_2$O (7%) | 90-95° C. | 18% |
| 0.1M HCl-EtOH (1:2) | CeCl$_3$•7H$_2$O (8%) | 90-95° C. | 55% |
| 0.1M HCl-EtOH (1:3) | CeCl$_3$•7H$_2$O (8%) | 90-95° C. | 33% |
| 0.1M HCl-EtOH (2:3) | CeCl$_3$•7H$_2$O (10%) | 90-95° C. | 62% (starch 1.2 eq.) |
| 0.1M HCl | CeCl$_3$•7H$_2$O (10%) | 90-95° C. | 29% (starch 1.2 eq.) |
| 0.1M HCl-EtOH (2:3) | CeCl$_3$•7H$_2$O (8%) | 90-95° C. | 64% (starch 1.5 eq.) |
| 0.1M HCl-EtOH (1:1) | CeCl$_3$•7H$_2$O (8%) | 90-95° C. | 63% (starch 1.5 eq.) |
| 0.1M HCl-EtOH (1.5:1) | CeCl$_3$•7H$_2$O (10%) | 90-95° C. | 64% (starch 1.2 eq.) |
| 0.1M HCl-EtOH (2:1) | CeCl$_3$•7H$_2$O (10%) | 90-95° C. | 59% (starch 1.2 eq.) |

EXAMPLE 10

Glucose was reacted with 1.5 equivalents of PrAA, and 25 mol % Fe(OTf)$_3$ (with respect to glucose), in boiling ethanol, for 12 hours. The ethanol was then removed by evaporation. Water was added and the mixture was subsequently extracted with an organic solvent. Removal of solvent gave rise to an 88% yield of the bis-furan isopropyl ester.

EXAMPLE 11

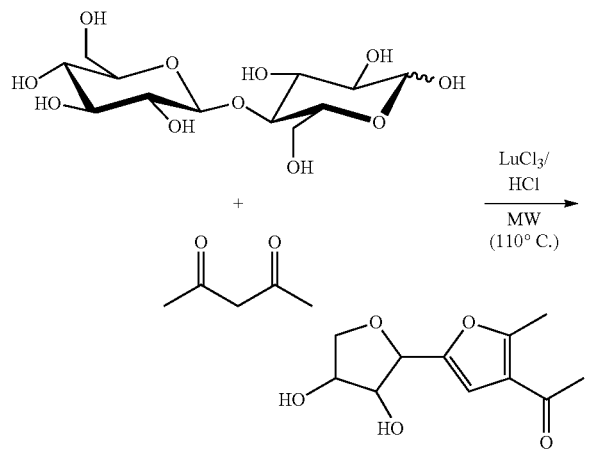

Method A: The dicarbonyl (1.266 mmol, 2.2 equivalent) was combined with the disaccharide (0.575 mmol, 1.0 equivalent), lutetium (III) trichloride (0.163 mmol, 0.3 equivalent), and 0.5 M HCl (0.35 mL), in 3.0 mL of water. The mixture was subjected to microwave conditions at 110° C. for 4 hours. Purification by silica gel chromatography gave rise to a mixture of the depicted compound and a compound of molecular weight 208 in 95% overall yield.

Method B: The dicarbonyl, water, HCl, LuCl$_3$, and the disaccharide was combined and the mixture was processed under microwave conditions at 110° C. for 4 hours. The mixture of the of the depicted compound and a compound of molecular weight 208 was obtained in 95% yield.

What is claimed:

1. A process of preparing a saturated hydrocarbon comprising:
    heating an oligosaccharide for time sufficient to form a depolymerized oligosaccharide mixture;
    combining the depolymerized oligosaccharide mixture with a dicarbonyl under conditions suitable to form an intermediate mixture; and
    adding hydrogen and a hydrogenation catalyst to the intermediate mixture under conditions suitable to form the saturated hydrocarbon.

2. The process of claim 1 wherein the dicarbonyl is methyl acetoacetate, ethyl acetoacetate, i-propyl acetoacetate, 2,4-pentanedione, n-propyl acetoacetate, malonate esters, cyanoacetates, or a mixture thereof.

3. The process of claim 2 wherein the dicarbonyl is 2,4-pentanedione.

4. The process of claim 1, wherein the saturated hydrocarbon is 3-ethylnonane.

5. The process of claim 1, wherein the hydrogenation catalyst is palladium/carbon.

6. The process of claim 1, wherein the heating is achieved using microwave radiation.

7. The process of claim 1, wherein the heating of the oligosaccharide to form the depolymerized oligosaccharide mixture is under acidic conditions.

8. The process of claim 7, wherein the acid conditions are achieved using hydrochloric acid, triflic acid, acetic acid, trifluoroacetic acid, or a combination thereof.

9. The process of claim 1, wherein the heating of the oligosaccharide to form the depolymerized oligosaccharide mixture is conducted in the presence of a Lewis acid catalyst or a Brønsted acid catalyst.

10. The process of claim 9, wherein the Lewis acid catalyst or the Brønsted acid catalyst is cerium chloride, iron chloride, lanthanum triflate, iron triflate, or a mixture thereof.

11. The process of claim 1, wherein the combining of the depolymerized oligosaccharide mixture with the dicarbonyl is conducted in the presence of a Lewis acid catalyst or a Brønsted acid catalyst.

12. The process of claim 11, wherein the Lewis acid catalyst or the Brønsted acid catalyst is cerium chloride, iron chloride, lanthanum triflate, iron triflate, or a mixture thereof.

* * * * *